(12) United States Patent
Myntti

(10) Patent No.: US 7,976,875 B2
(45) Date of Patent: *Jul. 12, 2011

(54) BIOFILM EXTRACELLULAR POLYSACCHARIDE SOLVATING SYSTEM

(75) Inventor: Matthew F. Myntti, St. Augustine, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/490,246

(22) Filed: Jun. 23, 2009

(65) Prior Publication Data

US 2009/0258086 A1 Oct. 15, 2009

Related U.S. Application Data

(62) Division of application No. 11/431,495, filed on May 10, 2006, now abandoned.

(51) Int. Cl.
  *A61K 33/00* (2006.01)
  *A61K 31/192* (2006.01)
  *A61K 31/194* (2006.01)
  *A61K 31/19* (2006.01)
  *A61K 33/42* (2006.01)
  *A61K 33/22* (2006.01)
  *A61K 31/60* (2006.01)

(52) U.S. Cl. ........ 424/605; 424/659; 424/666; 514/159; 514/557; 514/570; 514/574

(58) Field of Classification Search .................... None
See application file for complete search history.

(56) References Cited

U.S. PATENT DOCUMENTS

| | | |
|---|---|---|
| 3,422,186 A | 1/1969 | Sasmor |
| 4,002,775 A | 1/1977 | Kabara |
| 4,107,328 A | 8/1978 | Michaels |
| 4,323,551 A | 4/1982 | Parran, Jr. |
| 4,851,521 A | 7/1989 | Della Valle et al. |
| 4,902,281 A | 2/1990 | Avoy |
| 5,017,229 A | 5/1991 | Burns et al. |
| 5,145,664 A | 9/1992 | Thompson |
| 5,166,331 A | 11/1992 | Della Valle et al. |
| 5,208,257 A | 5/1993 | Kabara |
| 5,229,103 A | 7/1993 | Eagle et al. |
| 5,246,964 A | 9/1993 | Ueno |
| 5,290,552 A | 3/1994 | Sierra et al. |
| 5,326,567 A | 7/1994 | Capelli |
| 5,442,053 A | 8/1995 | Della Valle et al. |
| 5,480,658 A | 1/1996 | Melman |
| 5,575,815 A * | 11/1996 | Slepian et al. ................. 600/36 |
| 5,631,241 A | 5/1997 | Della Valle et al. |
| 5,644,049 A | 7/1997 | Giusti et al. |
| 5,662,913 A | 9/1997 | Capelli |
| 5,676,964 A | 10/1997 | Della Valle et al. |
| 5,709,546 A | 1/1998 | Waggoner |
| 5,763,410 A | 6/1998 | Edwardson et al. |
| 5,773,033 A | 6/1998 | Cochrum et al. |
| 5,895,781 A | 4/1999 | Neumiller et al. |
| 5,910,420 A | 6/1999 | Tuompo et al. |
| 5,925,334 A | 7/1999 | Rubin et al. |
| 6,001,870 A | 12/1999 | Henkel |
| 6,013,657 A | 1/2000 | Lavon et al. |
| 6,063,061 A | 5/2000 | Wallace et al. |
| 6,143,330 A | 11/2000 | Aaltonen et al. |
| 6,156,294 A | 12/2000 | Mautone |
| 6,156,792 A | 12/2000 | Hatton et al. |
| 6,203,822 B1 | 3/2001 | Schlesinger et al. |
| 6,224,857 B1 | 5/2001 | Romeo et al. |
| 6,248,371 B1 | 6/2001 | Domenico |
| 6,284,804 B1 | 9/2001 | Singh et al. |
| 6,342,251 B1 | 1/2002 | Illum et al. |
| 6,375,963 B1 | 4/2002 | Repka et al. |
| 6,395,295 B1 | 5/2002 | Hills et al. |
| 6,395,746 B1 | 5/2002 | Cagle et al. |
| 6,423,333 B1 | 7/2002 | Stedronsky et al. |
| 6,423,694 B1 | 7/2002 | Drutz et al. |
| 6,541,460 B2 | 4/2003 | Petito |
| 6,533,749 B1 | 7/2003 | Mitusina et al. |
| 6,610,314 B2 | 8/2003 | Koenig et al. |
| 6,616,913 B1 | 9/2003 | Mautone |
| 6,623,513 B2 | 9/2003 | Biel |
| 6,676,930 B2 | 1/2004 | Mautone |
| 6,685,697 B1 | 2/2004 | Arenberg et al. |
| 6,686,346 B2 | 2/2004 | Nilsson et al. |

(Continued)

FOREIGN PATENT DOCUMENTS

EP 0 530 861 B1 3/1993

(Continued)

OTHER PUBLICATIONS

Banin et al "Chelator-Induced Dispersal and Killing of Pseudomonas aeruginosa Cells in a Biofilm," Applied and Environmental Microbiology, 72(3): 2064-2069 (Mar. 2006).*

(Continued)

*Primary Examiner* — David J Blanchard
*Assistant Examiner* — Suzanne Ziska
(74) *Attorney, Agent, or Firm* — IPLM Group, P.A.

(57) ABSTRACT

The invention provides a solvating system for the removal of biofilms which solvates the extracellular polysaccharide matrix holding it to a surface. The aqueous solvating system comprises water, a metal ion sequestering agent, and a solvating agent for an extracellular polysaccharide matrix, which is gentle enough to be used directly on human tissues, but which may also be used on hard or soft non-tissue surfaces to breakdown, and/or remove biofilms.

25 Claims, No Drawings

U.S. PATENT DOCUMENTS

| | | |
|---|---|---|
| 6,706,290 B1 | 3/2004 | Kajander et al. |
| 6,723,709 B1 | 4/2004 | Pressato et al. |
| 6,762,160 B2 | 7/2004 | Barbeau et al. |
| 6,812,196 B2 | 11/2004 | Rees et al. |
| 6,855,678 B2 | 2/2005 | Whiteley |
| 6,867,233 B2 | 3/2005 | Roselle et al. |
| 6,869,938 B1 | 3/2005 | Schwartz et al. |
| 6,891,037 B1 | 5/2005 | Hasler et al. |
| 6,919,348 B2 | 7/2005 | Wei |
| 6,936,579 B2 | 8/2005 | Urban |
| 6,953,772 B2 | 10/2005 | Lopes |
| 6,962,813 B2 | 11/2005 | Pier et al. |
| 6,989,195 B2 | 1/2006 | Anderson |
| 7,090,882 B2 | 8/2006 | Koeford et al. |
| 7,119,217 B2 | 10/2006 | Jiang et al. |
| 7,128,897 B2 | 10/2006 | Osbakken et al. |
| 7,220,431 B2 | 5/2007 | Sawchuk et al. |
| 7,238,363 B2 | 7/2007 | Mansouri et al. |
| 7,244,841 B2 | 7/2007 | Love et al. |
| 7,341,983 B2 | 3/2008 | Pedersen et al. |
| 7,410,480 B2 | 8/2008 | Muni et al. |
| 7,446,089 B2 | 11/2008 | Singh et al. |
| 7,494,963 B2 | 2/2009 | Ahmed et al. |
| 7,544,192 B2 | 6/2009 | Eaton et al. |
| 7,714,011 B2 | 5/2010 | Clarot et al. |
| 2001/0051613 A1 | 12/2001 | Illum et al. |
| 2002/0022588 A1 | 2/2002 | Wilkie et al. |
| 2002/0187918 A1 | 12/2002 | Urban |
| 2003/0079758 A1 | 5/2003 | Siegel et al. |
| 2003/0083219 A1 | 5/2003 | Rees et al. |
| 2003/0133883 A1 | 7/2003 | Finnegan et al. |
| 2003/0139382 A1 | 7/2003 | Wall et al. |
| 2004/0101506 A1 | 5/2004 | Fust |
| 2004/0143001 A1 | 7/2004 | Love et al. |
| 2004/0204399 A1 | 10/2004 | Osbakken et al. |
| 2004/0214753 A1 | 10/2004 | Britten et al. |
| 2005/0003007 A1 | 1/2005 | Boix et al. |
| 2005/0032668 A1 | 2/2005 | Pedersen et al. |
| 2005/0042240 A1 | 2/2005 | Utterberg et al. |
| 2005/0043706 A1 | 2/2005 | Eaton et al. |
| 2005/0064508 A1 | 3/2005 | Belcher et al. |
| 2005/0080396 A1 | 4/2005 | Rontal |
| 2005/0106728 A1 | 5/2005 | Burgess et al. |
| 2005/0147679 A1 | 7/2005 | Petito et al. |
| 2005/0220895 A1 | 10/2005 | Bucalo et al. |
| 2005/0226937 A1 | 10/2005 | O'Hagan et al. |
| 2005/0244339 A1 | 11/2005 | Jauering et al. |
| 2005/0282722 A1 | 12/2005 | McReynolds et al. |
| 2006/0003008 A1 | 1/2006 | Gibson et al. |
| 2006/0018945 A1 | 1/2006 | Britigan et al. |
| 2006/0035808 A1 | 2/2006 | Ahmed et al. |
| 2006/0045850 A1 | 3/2006 | Namburi et al. |
| 2006/0051385 A1* | 3/2006 | Scholz .................. 424/405 |
| 2006/0106361 A1 | 5/2006 | Muni et al. |
| 2006/0205621 A1* | 9/2006 | Borazjani et al. ......... 510/161 |
| 2006/0210605 A1 | 9/2006 | Chang et al. |
| 2007/0207192 A1 | 9/2007 | Holl et al. |
| 2007/0264310 A1 | 11/2007 | Hissong et al. |
| 2007/0264342 A1 | 11/2007 | Oliver et al. |
| 2007/0264353 A1 | 11/2007 | Myntti et al. |
| 2008/0010947 A1 | 1/2008 | Huang et al. |
| 2008/0248558 A1 | 10/2008 | Deinhammer et al. |
| 2009/0005339 A1* | 1/2009 | Scholz et al. ............ 514/53 |
| 2010/0240770 A1 | 9/2010 | Qi et al. |

FOREIGN PATENT DOCUMENTS

| | | |
|---|---|---|
| EP | 1 374 856 A1 | 1/2004 |
| FR | 2 710 529 A1 | 4/1995 |
| JP | 52-007428 | 1/1977 |
| RU | 222 8203 | 5/2004 |
| SU | 1128917 A1 | 12/1984 |
| SU | 1699430 A1 | 12/1991 |
| WO | WO 94/05330 | 3/1994 |
| WO | WO 97/38698 | 10/1997 |
| WO | WO 98/09622 A1 | 3/1998 |
| WO | WO 99/27905 A | 6/1999 |
| WO | WO 00/21510 | 4/2000 |
| WO | WO 03/061579 A2 | 7/2003 |
| WO | WO 03/092745 A1 | 11/2003 |
| WO | WO 2004/009143 A1 | 1/2004 |
| WO | WO 2004/024187 A2 | 3/2004 |
| WO | WO 2005/000029 A2 | 1/2005 |
| WO | WO 2005/089670 A1 | 9/2005 |
| WO | WO 2006/099386 A2 | 9/2006 |
| WO | WO 2008/097317 A1 | 8/2008 |

OTHER PUBLICATIONS

Chang, JAOCS. vol. 60, No. 3, Mar. 1983.*
Chang (JAOCS. vol. 60, No. 3, Mar. 1983.*
Banin et al ("Chelator-Induced Dispersal and Killing of Pseudomonas aeruginosa Cells in a Biofilm," Applied and Environmental Microbiology, 72(3): 2064-2069 (Mar. 2006).*
Stoeckli, Sandro J. et al., "A Prospective Randomized Double-Blind Trial of Fibrin Glue for Pain and Bleeding After Tonsillectomy", Laryngoscope 109: pp. 652-655, (Apr. 1999).
Granick Mark MD et al., "Toward a common language: surgical wound bed preparation and debridement", Wound Repair and Regeneration, 14, S1-S10, © the Wound Healing Society, (2006).
Stetter, Christopher et al., "Skin grafting of a chronic leg ulcer with combined Versajet™-V.A.C. therapy", XP-002566870 Case Reports, JDDG, 4:739-742 (2006).
Nagoba, B.S. et al., A Simple and Effective Approach for the Treatment of Chronic Wound Infections Caused by Multiple Antibiotic Resistant *Escherichia coli*, Journal of Hospital Infection, 69:177-180 (2008).
Plateltex, "Reduce fibrosis-Reducing scarring-Autologous Platelets", accessed on Jan. 26, 2010 from: http://www.plateltex.com/lp_reduce_fibrosis.html.
"Medicine Encyclopedia" M., RLS, p. 561(2001)-Miramistin solution 0.01%.
Post, J.C., "Direct evidence of bacterial biofilms in otitis media", Laryngoscope 111(12):2083-94 (2001).
Ehrlich et al., "Mucosal Biofilm Formation on Middle-Ear Mucosa in the Chinchilla Model of Otitis Media", JAMA 287(13):1710-15 (2002).
Fergie, N. et al., "Is otitis media with effusion a biofilm infection?", Clin Otolaryngol Allied Sci. 29(1):38-46 (2004).
Ferguson B.J. and Stolz D.B., "Demonstration of biofilm in human bacterial chronic rhinosinusitis", Am J Rhinol 19:452-457, 2005.
Ramadan H.H., Sanclement J.A. and Thomas J.G., "Chronic rhinosinusitis and biofilms", Otolaryngol Head Neck Surg. 132:414-417, 2005.
Benninger M.S., Ferguson B.J., Hadley J.A., et al., "Adult chronic rhinosinusitis: Definitions, diagnosis, epidemiology, and pathophysiology", Otolaryngol Head Neck Surg 129 (3 suppl):S1-S32, 2003.
Nadel D.M., Lanza D.C., and Kennedy D.W., "Endoscopically guided cultures in chronic sinusitis", Am J Rhinol 12:233-241, 1998.
Stepanovic S, Vukovic D, Dakic I, et al., "A modified microtiter-plate test for quantification of staphylococcal biofilm formation", J Microbiol Methods 40:175-179, 2000.
Gotz F., "Staphylococcus and biofilms", Mol Microbiol 43:1367-1378, 2002.
Lethbridge-çejku M, Rose D, Vickerie J. Summary health statistics for US adults: National Health Interview Survey, 2004. National Center for Health Statistics. Vital Health Stat 2006;10 (228). Available: http://www.cdc.gov/nchs/fastats/sinuses.htm.
Rosiak, J.M. et al., "Radiation Formation of Hydrogels For Biomedical Purposes. Some Remarks And Comments", Radiat. Phys. Chem. vol. 46, No. 2, pp. 161-168, 1995.
Costerton J.W., Stewart P.S. and Greenberg E.P., "Bacterial biofilms: A common cause of persistent infections", Science 284:1318-1322, 1999.
Morris D.P. and Hagr A., "Biofilm: Why the sudden interest?" J Otolaryngol 34(suppl 2):S56-S5, 2005.
Hall-Stoodley L, Hu F.Z., Gieseke A, et al., "Direct detection of bacterial biofilms on the middle-ear mucosa of children with chronic otitis media." JAMA 296:202-211, 2006.

Sanderson A.R., Leid J.G., and Hunsaker D., "Bacterial biofilms on the sinus mucosa of human subjects with chronic rhinosinusitis", Laryngoscope 116:1121-1126 (2006).

Sanclement J.A., Webster P., Thomas J., and Ramadan H.H., "Bacterial biofilms in surgical specimens of patients with chronic rhinosinusitis", Laryngoscope 115:578-582, 2005.

Bendouah Z., Barbeau J., Hamad W.A., and Desrosiers M., "Biofilm formation by Staphylococcus aureus and Pseudomonas aeruginosa is associated with an unfavorable evolution after surgery for chronic sinusitis and nasal polyposis", Otolaryngol Head Neck Surg. 134:991-996, 2006.

Bhattacharyya N., and Kepnes L.J., "The microbiology of recurrent rhinosinusitis after endoscopic sinus surgery", Arch Otolaryngol Head Neck Surg. 125:1117-1120, 1999.

Cryer J., Schipor I., Perloff J.R., and Palmer J.N., "Evidence of bacterial biofilms in human chronic sinusitis", ORL J Otorhinolaryngol Relat Spec 66:155-158, 2004.

Meltzer E.O., Hamilos D.L., Hadley J.A., et al., "Rhinosinusitis: Establishing definitions for clinical research and patient care", J Allergy Clin Immunol 114(suppl):S155-S212, 2004.

Chiu A.G., and Kennedy D.W., "Surgical management of chronic rhinosinusitis and nasal polyposis: a review of the evidence", Curr Allergy Asthma Rep 4:486-489, 2004.

Bhattacharyya N., "Clinical outcomes after endoscopic sinus surgery", Curr Opin Allergy Clin Immunol 6:167-171, 2006.

Wormald P.J., Psaltis A., and Ha K., "A sheep model for the study of biofilms in sinusitis", In Programs and abstracts of the 52nd Annual Meeting of the American Rhinologic Society, Toronto, Ontario, Canada, Sep. 16, 2006.

Anglen J.O., Apostoles S., Christensen G., and Gainor B., "The efficacy of various irrigation solutions in removing slime-producing Staphylococcus", J Orthop Trauma 8:390-396, 1994.

Chole, Richard A. and Faddis, Brian T., Evidence for Microbial Biofilms in Cholesteatomas, Arch Otolaryngol Head and Neck Surg. 2002; 128: 1129-1133. Downloaded Apr. 17, 2007 from Medtronic Xomed at www.archoto.com.

Desrosiers M. Refractory chronic rhinosinusitis: pathophysiology and management of chronic rhinosinusitis persisting after endoscopic sinus surgery. Curr Allergy Asthma Rep 2004;4:200-7.

Smith TL, Batra PS, Seiden AM, Hannley M. Evidence supporting endoscopic sinus surgery in the management of adult chronic sinusitis: a systematic review. Am J Rhinol 2005;19:537-43.

Perloff Jr, Palmer JN. Evidence of bacterial biofilms on frontal recess stents in patients with chronic rhinosinusitis. Am J Rhinol 2004;18:377-80.

Wright ED, Frenkiel S. Infectious adult rhinosinusitis: etiology, diagnosis, and management principles. J Otolaryngol 2005;34(suppl 1):S7-13.

Luong A, Marple BF. Sinus surgery: indications and techniques. Clin Rev Allergy Immunol 2006;30:217-22.

Abdi-Ali A, Mohammadi-Mehr M, Agha Alaei Y. Bactericidal activity of various antibiotics against biofilm-producing Pseudomonas aeruginosa. Int J Antimicrob Agents;27:196-200, 2006.

Jefferson KK, Goldmann DA, Pier GB. Use of confocal microscopy to analyze the rate of vancomycin penetration through Staphylococcus aureus biofilms. Antimicrob Agents Chemother 2005;49:2467-73.

Walters MC 3rd, Roe F, Bugnicourt A, Franklin MJ, Stewart PS. Contributions of antibiotic penetration, oxygen limitation, and low metabolic activity to tolerance of Pseudomonas aeruginosa biofilms to ciprofloxacin and tobramycin. Antimicrob Agents Chemother 2003;47:317-23.

Palmer JN. Bacterial biofilms: do they play a role in chronic sinusitis? Otolaryngol Clin N. Am 2005;38:1193-1201.

Donlan RM. Biofilms: microbial life on surfaces. Emerg Infect Dis 2002;8:881-90.

Potera C. Forging a link between biofilms and disease. Science 1999;283:1837, 1839.

Post JC, Stoodley P, Hall-Stoodley L, Ehrlich GD. The role of biofilms in otolaryngologic infections. Curr Opin Otolaryngol Head Neck Surg 2004;12:185-90.

Tonnaer EL, Graamans K, Sanders EA, Curfs JH. Advances in understanding the pathogenesis of pneumococcal otitis media. Pediatr Infect Dis J 2006;25:546-52.

Rayner MG, Zhang Y, Gorry MC, Chen Y, Post CJ, Ehrlich GD. Evidence of bacterial metabolic activity in culture-negative otitis media with effusion. JAMA 1998;279:296-9.

Dingman JR, Rayner MG, Mishra S, Zhang Y, Ehrlich Md, Post JC, et al. Correlation between presence of viable bacteria and presence of endotoxin in middle-ear effusions. J Clin Microbiol 1998;36:3417-9.

Perloff JR, Palmer JN. Evidence of bacterial biofilms in a rabbit model of sinusitis. Am J Rhinol 2005;19:1-9.

Chiu A, Antunes M, Feldman M, Cohen N. Dose-dependent effects of topical tobramycin in an animal model of Pseudomonas sinusitis. In: Programs and abstracts of the 52nd Annual Meeting of the American Rhinologic Society; Sep. 16, 2006; Toronto, ON, Canada.

Witterick IJ, Kolenda J. Surgical management of chronic rhinosinusitis. Immunol Allergy Clin N Am 2004;24:119-34.

Lieu JE, Piccirillo JF. Methodologic assessment of studies on endoscopic sinus surgery. Arch Otolaryngol Head Neck Surg 2003;129:1230-5.

Lavigne F, Tulic MK, Gagnon J, Hamid Q. Selective irrigation of the sinuses in the management of chronic rhinosinusitis refractory to medical therapy: a promising start. J Otolaryngol 2004;33:10-16.

Protein Polymer Technologies Product Research infomation dated Feb. 3, 2006, 2 pages, downloaded from the Internet Archive on Dec. 15, 2009 at: http://web.archive.org/web/20060328113942/www.ppti.com/Market/Research.html.

Gross Charles W., et al., "Autologus Fibrin Sealant Reduces Pain After Tonsillectomy", The Laryngoscope, Lippincott Williams & Wilkins, Inc., Philadelphia (2001), The American Laryngological, Rhinological and Otological Society, Inc., Laryngoscope 111, pp. 259-263, Feb. (2001).

Vaiman Michael et al., "Fibrin Sealant Reduces Pain After Tonsillectomy: Prospective Randomized Study", Department of Otolaryngology, Assaf Harofe Medical Center and Sackler Faculty of Medicine Tel Aviv University, Tel Aviv, Israel, Annals of Otology Rhinology & Laryngology 115 (7), pp. 483-489 (2006).

Kitajiri et al., "Relief of Post-Tonsillectomy Pain by Release of Lidocaine From Fibrin Glue", The Laryngoscope, Lippincott Williams & Wilkins, Inc., Philadelphia (2001), The American Laryngological: Rhinological and Otological Society, Inc., Laryngoscope 111, pp. 642-644, Apr. (2001).

Yamada et al., "Chitosan Based Water-Resistant Adhesive. Analogy to Mussel Glue", *Biomacromolecules* 2000, 1 (2), pp. 252-258 (Apr. 13, 2000).

* cited by examiner

BIOFILM EXTRACELLULAR POLYSACCHARIDE SOLVATING SYSTEM

CROSS-REFERENCE TO RELATED APPLICATION

This application is a Divisional of application Ser. No. 11/431,495 filed May 10, 2006, the disclosure of which is incorporated by reference.

THE FIELD OF THE INVENTION

The present invention relates generally to the field of biofilm removal and more specifically to a solvating system for the solvation and removal of biofilms. The solvating system may be used on a variety of affected surfaces, including human or animal tissue, medical devices, water systems, and the like. The solvating system is especially beneficial for use on human tissue to remove biofilms which cause chronic conditions such as rhinosinusitis.

BACKGROUND OF THE INVENTION

Biofilms are formed by bacteria in aqueous environments, which interact with the surfaces to which they are exposed to form surface colonies and films which continue to adhere to the surfaces and grow. More specifically, the bacteria produce extensive exopolysaccharide or extracellularpolysaccharide polymers (EPS or ECPS) that keep them attached to the surfaces and form living films thereon, frequently called "biofilms". These biofilms can be formed on a variety of surfaces, including human tissues, medical devices, dental office equipment, counters, pipes and the like. Biofilms coat the surface and become a living colony for the continued proliferation of microorganisms, and protection of the microorganisms from removal and from conditions which might destroy the microorganisms. Biofilms are much more difficult to remove than bacteria in the plaktonic state, and the bacterial contamination of the biofilms from surfaces or tissue are thus much more difficult to eliminate. Biofilms in this state are extremely resistant to many antibiotics and biocides.

When present on human tissues, biofilms can cause chronic conditions from which many persons today suffer. Such conditions include rhinosinusitis, where biofilms are attached within the nasal passages and sinuses, infiltrating and protecting the underlying pathogenic bacteria and preventing them from being dislodged from their surfaces, and immune system disorder symptoms where biofilms have coated bodily tissues and surfaces such as joints or nerves in a manner which impairs the normal function thereof. Additionally, enclosure of implants or surgical appliances with biofilms may lessen their effectiveness.

Previous strategies for removal of biofilms have focused on both removal and destruction of bacteriums in the biofilm. Products for such cleansing, such as biocides, disinfectants and the like for use in such areas may be caustic and employ agents that can damage human skin, and especially non-dermal human tissues upon contact and therefore cannot be used to remove biofilms from human orifices and tissues. Methods of cleaning and disinfecting such surfaces effectively for biofilms may also involve large dosages, and long periods of contact with the surface, e.g., soaking biofilm contaminated surfaces for 12-24 hours, which is impractical for preoperative and postoperative situations and for many surfaces and devices as well as being impossible for use on or with most contaminated human tissues.

Methods of removal of biofilms from human tissues such as sinuses to flush them from the system have included mechanical debridement of the tissues and/or surgical opening of sinuses to allow for drying and subsequent removal of the biofilm. Such methods damage the tissues and require healing periods, and further present opportunities for new bacteria to contact the surfaces and cause infections and new placement of biofilms. Antibiotics have also been attempted but, while they are effective against plaktonic bacteria, they have been only marginally effective against biofilms, and then only when administered in large dosages, which may be otherwise undesirable for the patient or living tissues.

It would be desirable to have a solvating system for removing biofilms from human tissues which would meet biocompatibility requirements for contact with human tissue, and yet be effective in removal of such biofilms from tissues and bodily orifice linings such as nasal orifices, sinuses, oral tissues, for removal from implants or other appliances attached to bodily tissues and the like. Such desirable solvating systems would preferably be effective in small dosages for short periods of application. It would also be desirable for such solvating system to be further useful to dislodge biofilms attached to non-tissue surfaces in environmental locations such as medical devices and water systems, dental equipment and the like.

It has now been discovered that a solvating system comprising an alkali, metallic, or metal ion sequestering agent and a solvent or surfactant is surprisingly effective in removal of biofilms such as polysaccharides from human tissue while being gentle enough for application directly onto such tissues.

SUMMARY OF THE INVENTION

The invention provides a solvating system for the breakdown and/or removal of biofilm matrices from human tissue surfaces and nonhuman surfaces.

More specifically, the invention provides an aqueous solvating system for the breakdown of the biofilm's extracellular polysaccharide matrix, and consequent detachment/removal of biofilms from the surface to which it is attached or adhered. The solvating system of the invention comprises a metal ion sequestering agent and a solvating agent for the extracellular polysaccharide matrix selected from a solvent or a surfactant.

In one embodiment, the invention includes an aqueous solvating system comprising water or saline, a metal ion sequestering agent and a solvating agent selected from the group consisting of a solvent and a surfactant.

In another embodiment, the solvating system of the invention comprises metal ion sequestering agent selected from the group consisting of a mild acid having a molarity of at least about 0.05 molar.

In one embodiment, the metal ion sequestering agent is a mild acid having a molarity of at least about 0.05 molar wherein the metal ion is selected from alkali metals, alkaline earth metals, and iron.

In another embodiment, the solvating system comprises a solvating agent for the extracellular polysaccharide matrix selected from the group consisting of anionic surfactants, nonionic surfactants, cationic surfactants and zwitterionic surfactants.

The invention also provides a method of use for the solvating system comprising delivery to the affected location by power spray or lavage.

These terms when used herein have the following meanings.

1. The term "sequestering agent" means a chemical that will combine with another material, especially a metal ion, to prevent the material from coming out of solution.

2. The term "metal ion sequestering agent" means a sequestering agent that will combine with metal ions such as iron, alkali metals, alkaline earth metals, and the like to keep the metals in solution. In order of increasing atomic number the alkaline earth metals are beryllium, magnesium, calcium, strontium, barium, and radium. Alkali metals include sodium, potassium, rubidium, cesium, and francium.

3. The terms "attached" and "adhered" as used herein means that the biofilm is established on the surface which it coats or covers, and that the biofilm has some resistance to removal from the surface, whether the surface is living tissue or a nonliving surface. As the nature of this relationship is complex and poorly understood, no particular method of adherence or attachment is intended by such usage.

4. The term "solvating" means to form a solution consisting of the solvent and the solvate.

5. The term "removal of biofilms" means that at least a significant amount of the biofilm present on a surface is placed into suspension and no longer resides on the surface.

All weights, amounts and ratios herein are by weight, unless otherwise specifically noted.

DETAILED DESCRIPTION OF THE PREFERRED EMBODIMENTS

The following detailed description describes certain embodiments and is not to be taken in a limiting sense. The scope of the present invention is defined by the appended claims.

The invention provides an aqueous solvating system for the breakdown of the biofilm's extracellular polysaccharide matrix, and consequent detachment or removal of biofilms from the surface to which it is attached or adhered. The solvating system of the invention comprises a metal ion sequestering agent and a solvating agent for the extracellular polysaccharide matrix selected from a solvent or a surfactant.

The invention is biocompatible, and may be used directly on human tissue as well as other non-living surfaces. It is advantageous in that it contains no biocides which could be potentially harmful to human tissues.

Another advantage of the solvating system invention is that it is low viscosity which makes for easy delivery to the desired surface by means of lavage, misting, spray application, mopping, administering in droplets, and also easy removal by subsequently flushing, rinsing, and/or draining from orifices such as nasal passages or from other surfaces. In one embodiment, the solvating system has a pH of from greater than about 5 to about 8.5.

The sequestering agent is a metal ion sequestering agent, generally a mild acid of high molarity. Useful acids include citric acid, mandelic acid, 2-ketoglutaric acid, acetic acid, iminodiacetic acid, mucic acid, glycolic acid, fumaric acid, lactic acid, aspartic acid, phosphoric acid, pyruvic acid, chloroacetic acid, oxalic acid, oxamic acid, malic acid, dichloroacetic acid, phenylacetic acid, benzylic acid, maleic acid, succinic acid, chloromandelic acid, glutamic acid, nitrilotriacetic acid, boric acid, adipic acid, formic acid, glucuronic acid, salicylic acid, benzoic acid, benzoyl acid, formic acid, phthalic acid, ketopimelic acid, and hydrochloric acid.

Applicable metal ions which may be sequestered include alkali metals, alkaline earth metals, iron, and the like. In one embodiment the metal ion sequestering agent is an alkaline earth metal or alkali metal sequestering agent. The sequestering agent generally has a molarity of at least about 0.05 molar, preferably from about 0.05 to about 0.35 molar.

The solvating system further includes a solvating agent selected from a surfactant or solvent. Useful solvating agents include surfactants such as alkyl sulfates, alkyl sulfonates and aryl sulfonates. The surfactant is generally present in a strength of from about 0.001 to about 0.69 molar, preferably from about 0.025 to about 0.130 molar, and in an amount of from about 0.5% to about 20% of the weight of the solution.

The solvating agent may be selected from various surfactants, such as anionic surfactants, nonionic surfactants, cationic surfactants and zwitterionic surfactants. Useful anionic surfactants include but are not limited to, sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate, and sodium glycodeoxycholate. Useful cationic surfactants include but are not limited to hexadecylpyridinium chloride monohydrate, and hexadecyltrimethylammonium bromide. Useful nonionic surfactants include but are not limited to polyoxyethyleneglycol dodecyl ether, N-decanoyl-N-methylglucamine, Digitonin, n-dodecyl B-D-maltoside, octyl B-D-glucopyranoside, octylphenol ethoxylate, polyoxyethylene (8) isooctyl phenyl ether, polyoxyethylene sorbitan monolaurate, and polyoxyethylene (20) sorbitan monooleate. Useful zwitterionic surfactant include but are not limited to 3-[(3-cholamidopropyl) dimethylammonio]-2-hydroxy-1-propane sulfonate, 3-[(3-cholamidopropyl) dimethylammonio]-1-propane sulfonate, 3-(decyldimethlammonio) propanesulfonate inner salt, and N-dodecyl-N,N-dimethyl-3-ammonio-1-propanesulfonate. In one embodiment, the surfactant is sodium lauryl sulfate.

While not wishing to be bound by theory, it is believed that the metal ion sequestering material removes the ion which bridges the extracellular polysaccharide matrix and binds the polymer chains together. The solvating agent then first surrounds the unbound polymers and suspends them, breaking down the matrix, and subsequently solvates the unbound polymers, bringing them into solution where they can be easily flushed from the tissues or surfaces with the aqueous solvating solution.

Where desirable to both remove the biofilm and destroy the microorganisms contained therein, the solvating system of the invention may further include medicaments such as antibiotics, which will be much more effective against the microorganisms present after the extracellular polysaccharide matrix has been broken down into unbound polymers, suspended and/or solvated.

The solvating system may further include a buffer in order to provide a solution at the proper pH for contacting human tissue. Where desirable, the buffer may comprise up to about 25% of the active ingredients of the solution. Useful buffers include, but are not limited to potassium chloride, glycine, potassium hydrogen phthalate, sodium acetate, potassium hydrogen phthalate, barbitone sodium, and sodium citrate.

Where treatment of tissues is also desirable, the solvating system of the invention may include further pharmaceutical agents in appropriate dosages such as analgesics, steroids, and the like.

For comfort and ease of use in human patients, the solvating system may further include flavoring agents and sweetening agents including but not limited to, oil of peppermint, spearmint, wintergreen, clove, eucalyptus, cinnamon, lemon, lime and orange, cherry, sucrose, lactose, maltose, sorbitol, xylitol, sodium cyclamate, saccharine, and the like.

Additional adjuvants may include antioxidants, buffering agents, coloring agents, and the like, in amounts that will not substantially interfere with the salvation of the extracellular polysaccharide and removal of the significant amounts of the biofilm.

Although specific embodiments have been illustrated and described herein for purposes of description of the preferred embodiment, it will be appreciated by those of ordinary skill in the art that a wide variety of alternate and/or equivalent implementations calculated to achieve the same purposes may be substituted for the specific embodiments shown and described without departing from the scope of the present invention. Those with skill in the chemical, mechanical, electro-mechanical, electrical, pharmacological and computer arts will readily appreciate that the present invention may be implemented in a very wide variety of embodiments. This application is intended to cover any adaptations or variations of the preferred embodiments discussed herein. Therefore, it is manifestly intended that this invention be limited only by the claims and the equivalents thereof.

What is claimed is:

1. A method for the breakdown of a biofilm extracellular polysaccharide matrix, and for detachment or removal of the biofilm from a surface to which it is attached or adhered, which method comprises applying an aqueous solvating system solution to a biofilm on human or animal nasal passage or sinus tissue, or on a prosthetic system attached to such tissue, wherein said solution comprises water, an amount of metal ion sequestering agent and an amount of solvating agent for the extracellular polysaccharide matrix effective to break down such matrix and to detach or remove such biofilm from such surface, said solvating agent comprises a cationic or zwitterionic surfactant, and said solution has a pH greater than 5 and does not contain biocide harmful to such tissue.

2. A method according to claim 1 wherein said solution is applied to nasal passage tissue.

3. A method according to claim 1 wherein said solution is applied to sinus tissue.

4. A method according to claim 3 wherein said solution is applied to nasal passages or sinuses of persons with rhinosinusitius.

5. A method according to claim 1 wherein said solution is applied in the form of a spray, liquid, or gel.

6. A method according to claim 1 further comprising removing said solution by rinsing.

7. A method according to claim 1 further comprising removing said solution by allowing said solution to drain out of said tissue, by flushing or by aspiration.

8. A method according to claim 1 wherein said metal ion sequestering material removes an ion which bridges the biofilm extracellular polysaccharide matrix and binds polymer chains together.

9. A method according to claim 1 wherein said metal ion sequestering agent is a mild acid having a molarity of at least about 0.05 molar.

10. A method according to claim 1 wherein said metal ion sequestering agent has a molarity from about 0.05 to about 0.35 molar.

11. A method according to claim 1 wherein said metal ion sequestering agent comprises mandelic acid, 2-ketoglutaric acid, acetic acid, iminodiacetic acid, mucic acid, glycolic acid, fumaric acid, lactic acid, aspartic acid, phosphoric acid, pyruvic acid, chloroacetic acid, oxalic acid, oxamic acid, malic acid, dichloroacetic acid, phenylacetic acid, benzylic acid, maleic acid, succinic acid, chloromandelic acid, glutamic acid, nitrilotriacetic acid, boric acid, adipic acid, formic acid, glucuronic acid, salicylic acid, benzoic acid, benzoyl acid, phthalic acid, ketopimelic acid or hydrochloric acid.

12. A method according to claim 1 wherein said metal ion sequestering agent comprises citric acid.

13. A method according to claim 1 wherein said metal ion is selected from alkali metals, alkaline earth metals, and iron.

14. A method according to claim 1 further comprising a buffer.

15. A method according to claim 14 wherein said buffer comprises potassium chloride, glycine, potassium hydrogen phthalate, sodium acetate, potassium hydrogen phthalate, barbitone sodium or sodium citrate.

16. A method according to claim 14 wherein said metal ion sequestering agent comprises citric acid and said buffer comprises sodium citrate.

17. A method according to claim 14 wherein said buffer comprises up to about 25% of said solution.

18. A method according to claim 1 wherein said solvating agent is a cationic surfactant.

19. A method according to claim 1 wherein said solvating agent comprises hexadecyltrimethylammonium bromide.

20. A method according to claim 1 wherein said solvating agent is a zwitterionic surfactant.

21. A method according to claim 1 wherein said solvating agent comprises 3-[(3-cholamidopropyl)dimethylammonio]-2-hydroxy-1-propane sulfonate, 3-[(3-cholamidopropyl)dimethylammonio]-1-propane sulfonate, 3-(decyldimethlammonio) propanesulfonate inner salt or N-dodecyl-N,N-dimethyl-3-ammonio-1-propanesulfonate.

22. A method according to claim 1 wherein said solvating agent is present in said solution in a strength of about 0.001 to about 0.69 molar.

23. A method according to claim 1 wherein said solvating agent is present in said solution in a strength of about 0.025 to about 0.13 molar.

24. A method according to claim 1 wherein said solvating agent is about 0.5 to about 20 weight percent of said solution.

25. A method according to claim 1 wherein said solvating system has a pH up to about 8.5.

\* \* \* \* \*